United States Patent [19]

Slaugh et al.

[11] Patent Number: 4,658,078

[45] Date of Patent: Apr. 14, 1987

[54] VINYLIDENE OLEFIN PROCESS

[75] Inventors: Lynn H. Slaugh, Cypress; Galeon W. Schoenthal, Houston, both of Tex.

[73] Assignee: Shell Oil Company, Houston, Tex.

[21] Appl. No.: 896,700

[22] Filed: Aug. 15, 1986

[51] Int. Cl.$^4$ .............................................. C07C 2/26
[52] U.S. Cl. .................................... 585/512; 502/117; 585/511; 585/523
[58] Field of Search .................... 585/512, 511, 523; 502/117

[56] References Cited

U.S. PATENT DOCUMENTS

| 4,377,720 | 3/1983 | Langer | 502/117 |
| 4,404,344 | 9/1983 | Sinn et al. | 502/117 |
| 4,530,914 | 7/1985 | Ewen et al. | 502/117 |
| 4,542,199 | 9/1985 | Kaminsky et al. | 502/117 |

Primary Examiner—Asok Pal

[57] ABSTRACT

This invention relates to a process for dimerizing an alpha olefin to a vinylidene olefin which comprises contacting said alpha olefin with a catalyst comprising (a) cyclo(pentadienyl)zirconium or hafnium metallocene and (b) an aluminoxane wherein the atom ratio of Al to Zr or Hf in the catalyst ranges from about 1 to about 100.

6 Claims, No Drawings

VINYLIDENE OLEFIN PROCESS

FIELD OF THE INVENTION

This invention relates to a process for dimerizing alpha olefins to vinylidene olefins.

BACKGROUND OF THE INVENTION

Metallocene/alumoxane catalysts are known in the art for producing polymers from alpha olefins. Kaminsky, in *Chemical and Engineer News*, July 4, 1983, pp 29-30 and in Makromol *Chem., Rapid Commun.* 4, 417-421 (1983) discloses zirconium and titanium metallocenes in combination with alumoxanes as catalysts for the polymerization of olefins. Sinn et al in U.S. Pat. No. 4,404,344, issued Sep. 13, 1983 disclosed the use of zirconium metallocenes in combination with alumoxanes as olefins polymerization catalysts. European Pat. No. 128,045 discloses the use of at least two metallocenes in combination with alumoxane for polymerization of ethylene to products with a broad molecular weight distribution. Metallocenes disclosed are titanocenes, zirconocenes, hafnocenes and vanadocenes. Applicant's process, in contrast to the prior art, does not produce high molecular weight polymers, but rather low molecular weight dimers.

SUMMARY OF THE INVENTION

This invention is a process for dimerizing alpha olefins to vinylidene olefins by contacting the alpha olefins with a catalyst comprising a zirconium or hafnium metallocene and an alumoxane where the ratio of Al to Zr of Hf in the catalyst ranges from about 1 to about 100.

DETAIL DESCRIPTION OF THE INVENTION

The present invention is directed to a catalytic process for dimerizing alpha olefins into vinylidene olefin products. These products are useful as intermediates in preparing, for example, specialty detergents or lubricant additives.

In the present process, olefins of the general formula

RCH=CH$_2$ wherein R is alkyl, cycloalkyl or cycloalkyenyl and contains from 1 to about 30 carbon atoms are contacted with a metallocene/alumoxane catalyst to produce vinylidene olefin dimers of the following formula

CH$_2$=C(R)CH$_2$CH$_2$R

In general, R can not be too bulky or dimerization rates are inhibited. It is a routine matter to test a particular olefin with the catalysts used in the instant invention. Mixtures of alpha olefins can be used as starting materials, resulting in various cross dimerization products. Examples of starting olefins that have been utilized in the instant process are propylene, 1-butene, 1-hexene, 1-octene, 1-eicosene and 4-vinyl-1-cyclohexene. Neohexene was found to be unreactive alone but would cross dimerize with 1-octene. Styrene, internal olefins and α,ω-olefins were substantially unreactive in the instant process. Di-olefins, particularly conjugated di-olefins adversely affect the dimerization process.

The aluminoxanes (or alumoxanes) are well known in the art and are polymeric aluminum compounds which can be represented by the general formula (R-Al-O)$_n$ which is a cyclic compound and R(R-Al-O)$_n$AlR$_2$, which is a linear compound. In the general formula, R is a C$_1$-C$_5$ alkyl group such as, for example, methyl, ethyl, propyl, butyl and pentyl and n is an interger from 1 to about 20. Most preferably, R is methyl. Generally, in the preparation of aluminoxanes from, for example, trimethyl aluminum and water, a mixture of the linear and cyclic compounds are obtained.

The aluminoxanes can be prepared in various ways. Preferably, they are prepared by contacting water with a solution of trialkyl aluminum, such as, for example, trimethyl aluminum, in a suitable organic solvent such as benzene or an aliphatic hydrocarbon. The solvents that can be use are well-known and include the saturated aliphatic compounds such as butane, pentane, hexane, heptane, octane, isooctane, the purified kerosenes, etc.; the cycloaliphatics such as cyclobutane, cyclopentane, cyclohexane, cycloheptane, methylcycloheptane, dimethylcyclopentane, etc.; the alkenes, such as propylene, butene, 1-octene, etc.; the aromatic solvents such as benzene, toluene, xylene, etc.; and the like. The major requirements in the selection of a solvent are that it be liquid at reaction temperatures, that it does not react with water or the aluminoxanes or interfere with the desired dimerization reaction. The solvent must be oxygen-free. Hydroxy, ether, carboxyl, keto, and the like groups adversely affect aluminoxane production. A particularly suitably solvent is the olefin to be dimerized. For example, the alkyl aluminum is treated with water in the form of a moist solvent or the alkyl aluminum such as trimethyl aluminum can be desirably contacted with a hydrated salt such as hydrated copper sulfate or aluminum sulfate.

The aluminoxane can be prepared in the presence of a hydrated copper sulfate. This method comprises treating a dilute solution of trimethyl aluminun in, for example, toluene, with copper sulfate represented by the general formula CuSO$_4$.5H$_2$O. The ratio of copper sulfate to trimethyl aluminum is desirably about 1 mole of copper sulfate for 5 moles of trimethyl aluminum. The reaction is evidenced by the evolution of methane.

In general, the mole ratio of alkyl aluminum to water will be about 1:1 although variations of this ratio can occur without adversely affecting the aluminoxane product; i.e., the Al/water ratio can vary between about 0.66:1 to about 2:1, preferably between about 0.75:1 to about 1.25:1. A continuous method for producing aluminoxanes is given in U.S. Pat. No. 3,300,458, issued Jan. 24, 1967, incorporated herein by reference. Another suitable method involves the use of hydrated aluminum salts as given in U.S. Pat. No. 4,544,762, issued Oct. 1, 1985, incorporated herein by reference. Another suitable method is to use water which has been ultrasonically dispersed in a solvent as described in co-pending application Ser. No. 896,689 filed 8-15-1986 (T-2020), incorporated by reference herein or water which has been dispersed using high speed shearing as described in co-pending application Ser. No. 896,701, filed 8-15-1986 (T-2039), incorporated by reference herein.

The metallocenes used in the instant process have the general formula (cyclopentadienyl)$_2$MY$_2$ wherein M is zirconium or hafnium and each Y is individually selected from the group consisting of hydrogen, C$_1$-C$_5$ alkyl, C$_6$-C$_{20}$ aryl and halogen. Preferably Y is hydrogen, methyl or chlorine. It is understood that the Ys may be the same or different. For the purposes of this invention, included within the definition of the above cyclopentadienyl moiety is the lower alkyl($C_1$–$C_5$)-substituted, preferably the methyl-substituted cyclopentadienyl moiety. Other metallocenes such as those containing titanium, vanadium and niobium have been found not to work adequately in the instant process.

In general terms, the catalyst is prepared by adding the aluminoxane dissolved in an organic solvent preferably the solvent utilized to prepare the aluminoxane, to a well-stirred suspension of the metallocene in an organic solvent, which can be inert with respect to the catalyst system or, preferably can be the olefin which comprises the feed. When the stirred solution to which the aluminoxane has been added becomes homogeneous, the catalyst has been formed, and if the feed olefin has been used as solvent, the dimerization reaction commences.

Critical to the production of dimers rather than polymers is the selection of the particular metallocene and the particular atom ratio of Al to Zr in the catalyst. The atom ration of Al to Zr ranges from about 1:1 to about 100:1 preferably from about 1:1 to about 50:1. The ratio of Al to Zr in the catalyst effects the selectivity and conversion in opposite ways. As the Al/Zr ratio increases, the conversion and rate of reaction increases, but the selectivity to the dimer falls off. Also, as the carbon number of the feed olefin is increased, the Al/Zr ratio also must increase to provide equivalent results. Thus, a given Al/Zr ratio may be optimum for a given olefin feed, but not for a different olefin feed.

The dimerization reaction is carried out in a conventional fashion. It may be carried out continuously in a stirred tank reactor wherein olefin and catalyst are added continuously to a stirred tank and reactant, product and catalyst are removed from the stirred tank with the product separated and the catalyst and used reactant recycled back to the stirred tank. Alternatively, the reaction may be carried out in a batch reactor, wherein the catalyst, or the catalyst precursors, and reactant olefin are charged to an autoclave, and after being reacted for an appropriate time, product is separated from the reaction mixture by conventional means, such as distillation. The reaction is operable over a broad range of temperatures from about −60° C. to about 280° C., preferably in the range of about 0° C. to about 150° C.

Pressures are not critical and can range from about 1 to about 500 atmosphere or higher.

The invention will be further described by the following examples and Illustrative Embodiments which are provided for illustration and are not to be construed as limiting the invention.

EXAMPLE 1

A typical catalyst was prepared in a dry box by adding 4.6 g (16 millimoles (mmoles)) of 25% trimethyl aluminum is toluene to a magnetically stirred bottle containing 1.0 g (16 mmoles water) copper sulfate pentahydrate in 20 ml toluene. After 15 minutes the gas evolution slowed and slow stirring was started. At 1.5 hr the material was heated to 140° F. and cooled. The liquid was withdrawn and added to a 100 ml autoclave containing 0.29 g (1 mmole) bis(cyclopentadienyl)zirconium dichloride ($Cp_2ZrCl_2$). 25 Grams (0.6 mole) of propylene was charged to the autoclave, and the vessel heated at 40°–46° C. for 3 hours. The pressure rose to a maximum of 185 psig and dropped to a final pressure of 40 psig. The reaction product was removed and analyzed.

Conversion of the propylene was greater than 95%.

The weight percent selectivity to $C_6$ olefin was 95.8%, with 4.2% going to $C_9$ olefin.

NMR analysis of the $C_6$ showed 95.8%: 2 methyl-1-pentene; 1.8%: 2,3-dimethyl-1-butene; 2.3%: 2-methyl pentane; 0.1% : 2,3-dimethylbutane.

EXAMPLE 2

A catalyst was prepared as per example 1 (propylene experiment) except that the quantities were cut in half. The catalyst was added to 200 ml of 1-octene (1.23 moles) in a 500 ml r.b. flask fitted with a magnetic stirrer, a thermometer and a nitrogen purged stopcock for sample withdrawal. The flask was heated to about 33°–40° C. After 24 hrs the 1-octene weight % conversion was 94.8%; wt% selectivity to dimer was 92.6%; and trimer was 3.0%. Nmr showed the $C_{16}$ to be 96+wt% 2 hexyl-1-decene.

ILLUSTRATIVE EMBODIMENT I

Catalysts were prepared similar to Example 1 with varying Al:Zr ratios. These catalysts were prepared from methylaluminoxane (from trimethyl aluminum) and bis(cyclopentadienyl)zirconium dichloride and were used to dimerized propylene. The results are shown in Table I.

TABLE I

OLIGOMERIZATION OF PROPYLENE
CONDITIONS: 100 ml autoclave
~21–23 g propylene
20–33° C. reaction temperature
autogenic pressure
1 hour runs

| EXPT. NO. | MMOLES $Cp_2ZrCl_2$ | Al:Zr RATIO | CONV. % | RELATIVE WT % SELECTIVITY OF $C_6$–$C_{18}$ | | | | | % wt OF PROPYLENE TO >$C_{18}$, |
|---|---|---|---|---|---|---|---|---|---|
| | | | | $C_6$ | $C_9$ | $C_{12}$ | $C_{15}$ | $C_{18}$ | |
| 1 | 1 | 8 | 9.5 | 97 | 3 | | | | |
| 2 | 1 | 16 | 50 | 83.7 | 14 | 1.9 | 0.4 | | |
| 3 | 1 | 24 | 68.5 | 86.1 | 12.7 | 1 | 0.2 | | |
| 4 | 1 | 32 | 100 | 83.4 | 13.4 | 1.7 | 0.3 | | 5.2 |
| 5 | 0.5 | 64 | 92 | 66.9 | 23.5 | 4.8 | 0.9 | | 3.9 |
| 6 | 0.25 | 128 | 87 | 66.7 | 25.1 | 6.0 | 1.7 | 0.5 | 2.5 |
| 7 | 0.076 | 426 | 67 | 43 | 30.6 | 15.3 | 7.5 | 3.8 | |
| 8 | 0.055 | 600 | 58.8 | 30.9 | 26.7 | 21.8 | 13.0 | 7.6 | 13.5 (includes polymer) |

ILLUSTRATIVE EMBODIMENT II

Illustrative Embodiment 2 was repeated with a run time of 2 hours instead of 1 hour. The isomer composition of the dimer was determined. Results are shown in Table II.

dichloride and were used to dimerize 1-hexene. The results are shown in Table IV.

TABLE II

EFFECTS OF Al:Zr CATALYST COMPONENT RATIOS: PROPYLENE DIMERIZATION
TOLUENE SOLVENT: 20 ml
PROPYLENE: 25–27 g
CATALYST: $Cp_2ZrCl_2$ + methylaluminoxane
TEMP.: 35–47° C.
PRESSURE: Autogenic
REACTION TIME: 2 hrs.

| EXPT. NO. | Al:Zr ATOMIC RATIO | CONVERSION OF PROPYLENE, % | WEIGHT % SELECTIVITY TO VARIOUS DIMERS (NORMALIZED TO 100%) | | | |
|---|---|---|---|---|---|---|
| | | | 2-Me-1-PENTENE | 2,3-DI-METHYL-1-BUTENE | 2-Me-PENTANE | 2,3-DI-METHYL-BUTANE |
| 9[a] | 8:1 | 90 | 95.8 | 1.3 | 1.0 | 0.4 |
| 10[b] | 16:1 | 90 est. | 95.8 | 2.3 | 1.8 | 0.1 |
| 11[c] | 420:1 | 71 | 76 | 13 | 9 | 1 |

[a] Oligomer Composition: 97.6% $C_6$, 2.4% $C_9$, 0% $C_{12}$ (weight %).
[b] Oligomer Composition: 95.8% $C_6$, 4.2% $C_9$, 0% $C_{12}$ (weight %).
[c] Oligomer Composition: 30.3% $C_6$, 22.9% $C_9$, 23.1% $C_{12}$, 12.3% $C_{15}$, 7.8% $C_{18}$, 2.8% $C_{21}$, 0.87% $C_{24}$ (weight %).

TABLE IV

OLIGOMERIZATION OF 1-HEXENE
TOLUENE (SOLVENT): 30 ml
$Me_3Al$, 4 mmoles + $H_2O$, 5 mmoles
$Cp_2ZrCl_2$: VARIABLE
HEXENE: 400 mmoles
TEMPERATURE: 40° C.

| EXPT. NO. 17554 | TIME HRS | $Cp_2Zr_2Cl_2$ mmoles | Al:Zn ATOMIC RATIO | 1-HEXENE CONVERSION % | WT % SELECTIVITY | | | | |
|---|---|---|---|---|---|---|---|---|---|
| | | | | | 2-HEXENE | $C_7H_{14}$ | DIMER | TRIMER | TETRAMER |
| 16 | 1 | 2.0 | 2 | 13.3 | 8.2 | 4.3 | 87.5 | 1.0 | |
| | 2 | | | 34.6 | 5.9 | 2.1 | 88.6 | 3.5 | |
| 17 | 1 | 1.0 | 4 | 63.1 | 4.1 | 1.7 | 91.1 | 3.8 | |
| | 2 | | | 92.5 | 2.5 | 1.2 | 94.5 | 1.9 | |
| 18 | 1 | 0.5 | 8 | 80.8 | 4.7 | 1.8 | 88.3 | 5.2 | |
| 19 | 1 | 0.25 | 16 | 58.6 | 7.0 | 3.2 | 84.6 | 4.7 | 0.6 |
| | 2 | | | 84.2 | 5.5 | 2.2 | 89.2 | 3.0 | 0.2 |

ILLUSTRATIVE EMBODIMENT III

Catalysts were prepared similar to Example 1 with varying Al:Zr ratios. The catalysts were prepared from methylaluminoxane (from trimethyl aluminum) and bis(cyclopentadienyl)zirconium dichloride and were used to dimerize 1-octene. The results are shown in Table III.

ILLUSTRATIVE EMBODIMENT V

This embodiment illustrates the differences in reactivities as the carbon number of the feed increases. The catalysts were prepared from methylaluminoxane (from trimethyl aluminum) and bis(cyclopentadienyl)zirconium dichloride. The feeds were propylene, butene, 3-methyl-1-butene and 3,3-dimethyl-1-butene. The results are shown in Table V.

TABLE III

1-OCTENE[a] DIMERIZATION

| EXPT. NO. | Al:Zr ATOMIC RATIO | RXN TEMP. °C. | RXN TIME, HRS | CONVERSION 1-OCTENE | WT % SELECTIVITY | | | CONVERSION MOLES 1-OCTENE PER MOLE CATALYST |
|---|---|---|---|---|---|---|---|---|
| | | | | | 2-OCTENE | C16 DIMER | C24 TIMER | |
| 12[b] | 8 | 70 | 19 | 11.2 | 5.8 | 92.7 | 1.6 | 517 |
| 13[c] | 16 | 70 | 1 | 42.2 | 4.7 | 92.4 | 3.1 | 1088 |
| | | | 6 | 77.8 | 5.6 | 91.4 | 3.0 | 1914 |
| 14[d] | 16 | 40 | 6 | 26.4 | 5.0 | 90.2 | 4.8 | 4110 |
| | | | 24 | 66.9 | 4.2 | 90.6 | 5.2 | 4622 |
| | | | 118 | 75.2 | 4.3 | 90.8 | 4.9 | |
| 15[e] | 64 | 40–50 | 2 | 33.8 | 5.1 | 86.2 | 7.7 | 5786 |
| | | | 6 | 86.8 | 4.5 | 88.0 | 7.5 | |
| | | | 24 | 97.0 | 4.2 | 88.4 | 7.4 | |

[a] Obtained from Aldrich Chemical Company: 97% 1-octene, 0.07% 2-octene plus 2.93% unspecified.
[b] One mmole of I (bis(cyclopentadienyl)zirconium dichloride) and 4760 mmoles of octene feed.
[c] 0.5 mmole of I and 1230 mmoles of octene feed.
[d] 0.5 mmole of I and 3075 mmoles of active feed.
[e] 0.5 mmole of I and 2979 mmoles of active feed. The grams of 2-octene produced in 2 hours and 24 hours was 5.3 g and 12.8 g, respectively.

ILLUSTRATION EMBODIMENT IV

Catalysts were prepared similar to Example 1 with varying Al:Zr ratios. The catalysts were prepared similar to Example 1, from methylaluminoxane (from trimethyl aluminum) and bis(cyclopentadienyl)zirconium

TABLE V

RELATIVE REACTIVITIES
Toluene Solvent - 10 ml
Al:Zr atomic ratio - 16:1
Reaction Temp. - 28-35°
Reaction Time - 1.0 hr.

| Expt No. | Feed | MMoles | Wt. % Conversion |
| --- | --- | --- | --- |
| 20 | Propylene | 476 | 49.4 |
| 21 | 1-Butene | 475 | 41.9 |
| 22 | 3-Methyl-1-Butene | 484 | 23 |
| 23 | 3,3-Dimethyl-1-Butene | 480 | 0 |

ILLUSTRATIVE EMBODIMENT VI

Catalysts were prepared similar to Example 1 with differing alumninoxane precursors and bis(cyclopentadienyl)zirconium dichloride at a Al:Zr ratio of 16:1. The results are shown in Table VI.

TABLE VI

EFFECT OF STRUCTURE OF TRIALKYLALUMINUM ALUMINOXANE PRECURSOR
CONDITIONS: 100 ml AUTOCLAVE
21-25 g PROPYLENE
35-45° C. REACTION TEMP.
AUTOGENIC PRESSURE
16 MMOLES $R_3Al$ + 20 mmoles $H_2O$ FROM $CuSO_4.5H_2O$
1-0 MMOLE $Cp_2ZrCl_2$
Al:Zr ATOMIC RATIO 16:1

| EXPT. NO. | $R_3Al$ USED | RXN TIME HRS | CONVERSION OF PROPYLENE % | WT. % SELECTIVITY, NORMALIZED TO 100% | | | | 2-Me-1-PENTENE CONTENT OF DIMERIC MATERIAL |
| --- | --- | --- | --- | --- | --- | --- | --- | --- |
| | | | | DIMER $C_6$ | TRIMER $C_9$ | TETRAMER $C_{12}$ | PENTAMER $C_{15}$ | |
| 24 | $Me_3Al$ | 2 | 90 | 95.8 | 4.2 | — | — | 95.8 |
| 25 | $Et_3Al$ | 3 | 62 | 93.2 | 5.2 | 1.0 | 0.6 | 95.2 |
| 26 | $(i-Bu)_3Al$ | 6 | 39 | 98.4 | 1.6 | — | — | 90.0 |

ILLUSTRATIVE EMBODIMENT VII 0.5 Millimoles of bis(cyclopentadienyl)zirconium dimethyl, 4 millimoles of aluminoxane and 50 ml of 1-octene were heated in the stirred round bottomed flask at 40° C. for 1 hour. Analysis of the reaction product showed a 19.1 wt conversion of 1-octene with the selectivity (wt%) as follows: octene dimer=72.2 and octene trimer=19.7

ILLUSTRATIVE EMBODIMENT VIII

1 Millimole of bis(cyclopentadienyl)zirconium hydrogen chloride, 8 millimoles of aluminoxane and 0.47 moles of 1-butene were heated in an autoclave at 70° C. for 1 hour. Analysis of the reaction product showed a 20 %wt conversion of 1-butene with a selectivity as follows: dimer=96 %wt and trimer=4 %wt

ILLUSTRATIVE EMBODIMENT IX

1 Millimole of bis(cyclopentadianyl)zirconium hydrogen chloride, 4 millimoles of aluminoxane and 50 ml of 1-octene were heated in an autoclave at 40° C. for 1 hour. Analysts of the reaction product showed an 8 %wt conversion of the 1-octene with a selectivity to the dimer being 72 %wt and to the trimer being 1.5 %wt.

ILLUSTRATIVE EMBODIMENT X

In this illustrative embodiment various amounts of water was used to prepare the aluminoxane and the results on the dimerization catalysts were measured.

The catalysts were prepared as follows: 20 ml of dry toluene were placed in a bottled fitted with a nitrogen purge system and the bottle was placed in an ultrasonic bath (Branson). The ultrasonic was started and the designated amount of water was added through a hypodermic syringe. After a five minute period of sonification, 4 mmoles of trimethyl aluminum (as a 25 %wt solution in toluene) was added. After the reaction was completed (as evidenced by termination of gas evolution), 50 ml of 1-octene and 0.5 mmole of bis(cyclopentadienyl)zirconium dichloride was added and the mixtures was heated to 40° C. After 30 minute samples were removed for analysis. The results are shown in Table VIII.

TABLE VIII

EFFECT OF TRIMETHYL ALUMINUM: WATER RATIO ON 1-OCTENE CONVERSION

| Water, mmoles | Al/water | Wt. % Conversion of 1-Octene |
| --- | --- | --- |
| 3.0 | 0.75 | 37 |
| 3.2 | 0.8 | 57 |
| 3.6 | 0.9 | 72 |
| 3.9 | 0.975 | 67 |
| 4.0 | 1.0 | 49 |
| 4.2 | 1.05 | 29 |
| 4.7 | 1.175 | 12 |

We claim:

1. A process for dimerizing an alpha olefin of the general formula $RCH=CH_2$ where R is alkyl, cycloalkyl or cycloalkenyl with a carbon number ranging from 1 to about 30 to a vinylidene olefin which process comprises contacting said alpha olefin at a temperature ranging between about −60° C. to about 280° C. with a catalyst comprising (a) a metallocene having the general formula $(cyclopentadienyl)_2MY_2$ wherein M is zirconium or hafnium and each Y is individually selected from the group consisting of hydrogen, $C_1$-$C_5$ alkyl, $C_6$-$C_{20}$ aryl and halogen and (b) an alumoxane, wherein the atom ratio of aluminum to M in the catalyst ranges from about 1 to about 100.

2. The process of claim 1 wherein Y is hydrogen, methyl or chlorine.

3. The process of claim 2 wherein M is zirconium.

4. The process of claim 3 wherein the metallocene is bis(cyclopentadienyl)zirconium dichloride(I).

5. The process of claims 1, 2, 3 or 4 wherein the temperature ranges from about 0° C. to about 150° C.

6. The process of claims 1, 2, 3 or 4 wherein the atom ratio of aluminum to M ranges from about 1 to about 50.

* * * * *